US010968113B2

(12) United States Patent
Lytle et al.

(10) Patent No.: US 10,968,113 B2
(45) Date of Patent: Apr. 6, 2021

(54) LEAD EXPOSURE ASSESSMENT DEVICE

(71) Applicant: GOVERNMENT OF THE UNITED STATES AS REPRESENTED BY THE ADMINISTRATOR OF THE U.S. ENVIRONMENTAL, Washington, DC (US)

(72) Inventors: Darren Alan Lytle, Liberty Township, OH (US); Michael Reed Schock, Cincinnati, OH (US)

(73) Assignee: GOVERNMENT OF THE UNITED STATES AS REPRESENTED BY THE ADMINISTRATOR OF THE U.S. ENVIRONMENTAL PROTECTION AGENCY, Washington, DC (US)

( * ) Notice: Subject to any disclaimer, the term of this patent is extended or adjusted under 35 U.S.C. 154(b) by 194 days.

(21) Appl. No.: 16/125,039

(22) Filed: Sep. 7, 2018

(65) Prior Publication Data

US 2019/0100443 A1    Apr. 4, 2019

Related U.S. Application Data

(60) Provisional application No. 62/604,447, filed on Jul. 7, 2017.

(51) Int. Cl.
| *C02F 1/00* | (2006.01) |
| *C02F 1/28* | (2006.01) |
| *G01N 27/62* | (2021.01) |
| *G01N 33/18* | (2006.01) |
| *C02F 101/20* | (2006.01) |

(52) U.S. Cl.
CPC .............. *C02F 1/003* (2013.01); *C02F 1/283* (2013.01); *G01N 27/62* (2013.01); *G01N 33/1813* (2013.01); *C02F 2101/20* (2013.01); *C02F 2209/001* (2013.01); *C02F 2209/40* (2013.01); *C02F 2307/06* (2013.01); *E03C 2201/40* (2013.01)

(58) Field of Classification Search
CPC ...... C02F 1/003; C02F 1/283; C02F 2101/20; C02F 2209/001; C02F 2209/40; C02F 2307/06; E03C 2201/40; G01N 27/60; G01N 33/1813
See application file for complete search history.

(56) References Cited

U.S. PATENT DOCUMENTS

| 6,296,760 | B1 * | 10/2001 | Petty ...................... B01D 61/00 210/170.01 |
| 9,004,290 | B2 | 4/2015 | Tanner et al. |
| 2005/0263457 | A1 * | 12/2005 | Wilkins .................... C02F 1/74 210/748.11 |

(Continued)

*Primary Examiner* — Jennifer Wecker
(74) *Attorney, Agent, or Firm* — Stein IP, LLC

(57) ABSTRACT

The invention relates to a device and method to quantify the lead exposure of an aqueous feed to humans, remove lead from the aqueous feed, and identify the presence of lead service lines. The device includes an inlet to receive a lead-containing aqueous feed; an outlet to discharge a lead-depleted treated aqueous feed; and at least one cartridge containing sampling media positioned so that the lead-containing aqueous feed passes from the inlet and through the cartridge to produce the lead-depleted treated aqueous feed for discharge through the outlet.

12 Claims, 2 Drawing Sheets

(56) References Cited

U.S. PATENT DOCUMENTS

| | | | |
|---|---|---|---|
| 2007/0108056 A1* | 5/2007 | Nyberg | C02F 1/4602 204/554 |
| 2008/0023405 A1* | 1/2008 | Rawson | C02F 1/28 210/688 |
| 2010/0300974 A1* | 12/2010 | Pate | B01D 15/00 210/665 |
| 2012/0145640 A1* | 6/2012 | Davis | B01J 20/043 210/688 |
| 2017/0239597 A1* | 8/2017 | Foyteck | C02F 1/001 |

* cited by examiner

LEAD EXPOSURE ASSESSMENT DEVICE

CROSS-REFERENCE TO RELATED APPLICATIONS

This application claims the benefit of priority to U.S. Provisional Application No. 62/604,447, filed Jul. 7, 2017 in the U.S. Patent and Trademark Office. All disclosures of the document named above are incorporated herein by reference.

BACKGROUND OF THE INVENTION

Field of the Invention

The invention relates to a device and method for determining the average levels of certain contaminants in drinking water at the point-of-use (e.g., a drinking water tap). More specifically, the invention relates to a device and method for determining the average level of lead in drinking water at the point-of-use. In addition to determining the level of lead, the device removes lead and other contaminants at the point-of-use to minimize human exposure. Further, the invention relates to a device for assessing the presence of lead pipe drinking water service lines.

There is an important need to develop a drinking water sampling approach that attempts to address the question of lead exposure and the challenges associated with identifying lead service lines.

Lead contamination in drinking water remains a major environmental problem in America and throughout the world, as evidenced by the recent water crisis in Flint, Mich. and lead exposure discovered in Washington D.C. over a decade ago. While the health effects of lead are generally harmful to the entire population, young children, infants and fetuses are particularly at risk to lead exposure because the physical and behavioral effects of lead occur at lower exposure levels in children than in adults. A dose of lead that would have little effect on an adult may have a significant effect on a child. In children, low levels of exposure have been linked to damage to the central and peripheral nervous systems, learning disabilities, shorter stature, impaired hearing, and impaired formation and function of blood cells.

Lead can enter drinking water when lead service lines corrode and release lead to the drinking water, especially where the water is corrosive and corrosion control is not effective. Other lead containing plumbing materials (e.g., brass or chrome-plated brass faucets and fixtures, leaded solders, and galvanized pipe) may also release significant amounts of lead to drinking water and raise public health concerns. Older houses and public buildings (e.g., schools) built before 1986 are more likely to have lead pipes, fixtures and solder than newer structures.

The extent to which lead enters into water from the corrosion of pipes and plumbing systems is based on many factors, including the chemistry of the water (acidity and alkalinity), the types and amounts of minerals in the water, the amount of lead the water comes contact with, the temperature of the water, the amount of wear in the pipes, the length of time water stays in the pipes, the random nature of particulate lead release, and the presence of protective scales or coatings inside the plumbing materials. Furthermore, household water usage patterns impact the transport of lead from sources through household plumbing. Given the multiple causes of lead contamination and lead transport relationship to water usage, it is extremely difficult to predict the concentration of lead in the water at the point-of-use at any time or an average lead level over time.

While it is necessary to identify the presence of lead service lines and measure the average lead concentration at point-of-use over time, there is no water sampling device that does either. Adding the capability to also remove lead from the water, there is no single device currently available that fulfills all these needs. Moreover, existing methods of determining the amount of lead in drinking water require residents to follow complicated sampling protocols to try to represent an estimate of the amount of lead that flows from the tap as a result of typical water consumption at that location. Such methods do not accurately measure human exposure to lead at the source. Neither do they have a provision for removing lead from the water.

There is thus a real need to provide a device and a method to provide a non-invasive assessment of human lead exposure at a point-of-use and, at the same time, identify lead service lines and remove lead from the water. Other objects will also be apparent from the detailed description of the invention.

SUMMARY OF THE INVENTION

Broadly speaking, the invention is intended to serve three different purposes. First, the invention embraces a device and method to determine the average levels of lead (and possibly other contaminants) in an aqueous feed (e.g., drinking water at a faucet or tap) as well as cumulative exposure at said feed. Second, the device may be used to identify the presence of lead service lines. Third, the same device removes lead and other contaminants of concern (e.g., other metals) from the aqueous feed, thus providing health protection both during the monitoring period and during normal usage periods.

The objectives of the invention are realized, according to one aspect of the invention, by a device that includes an inlet to receive a lead-containing aqueous feed; an outlet to discharge a lead depleted treated aqueous feed; and at least one cartridge positioned so that the lead-containing aqueous feed passes from the inlet and through the cartridge to produce the lead-depleted aqueous feed for discharge through the outlet. The cartridge may contain lead removal and sampling media, and the device may be configured to quantify the average lead exposure of humans to the aqueous feed, to remove lead from the aqueous feed, and to identify the presence of lead service lines.

The lead may be particulate lead, soluble lead, or a mixture of both particulate and soluble lead. Other contaminants may also be present.

In one embodiment, the device may be attached to or located near the outlet section of a water dispensing faucet.

In one embodiment, the device may remove metals or other contaminants in addition to lead. Such metals may include but are not limited to copper, cadmium, zinc, and arsenic.

In one embodiment of the invention, the sampling media in the device comprises activated carbon, block carbon, resin-modified carbon, or mixtures of the same. Other suitable materials may be used (e.g., iron- or titanium-based media) in embodiments of the invention.

In one embodiment, the device further includes a flow totalizer meter configured to provide total flow information that passed through the media device during a designated period of time.

In another embodiment of the invention, the sampling media may be easily and safely extracted from the device for lead analysis. This will permit the accurate measurement of captured lead (or other contaminant for an analysis).

Another embodiment of the invention embraces a method of determining human exposure to lead in an aqueous feed over a designated time period, the method including the following steps: attaching the device described above to an aqueous feed outlet; determining the total flow of aqueous feed passing through the device over the designated time period; removing the sampling media from the device after the designated time period; determining the amount of lead collected in the sampling media over the designated time period; and calculating the average concentration of lead in the water by dividing the amount of lead by the total flow of aqueous feed. In another embodiment of the invention following the same series of steps, the calculated average lead concentration may be used to predict the likelihood an unseen lead service line is present.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

Figure 1A:
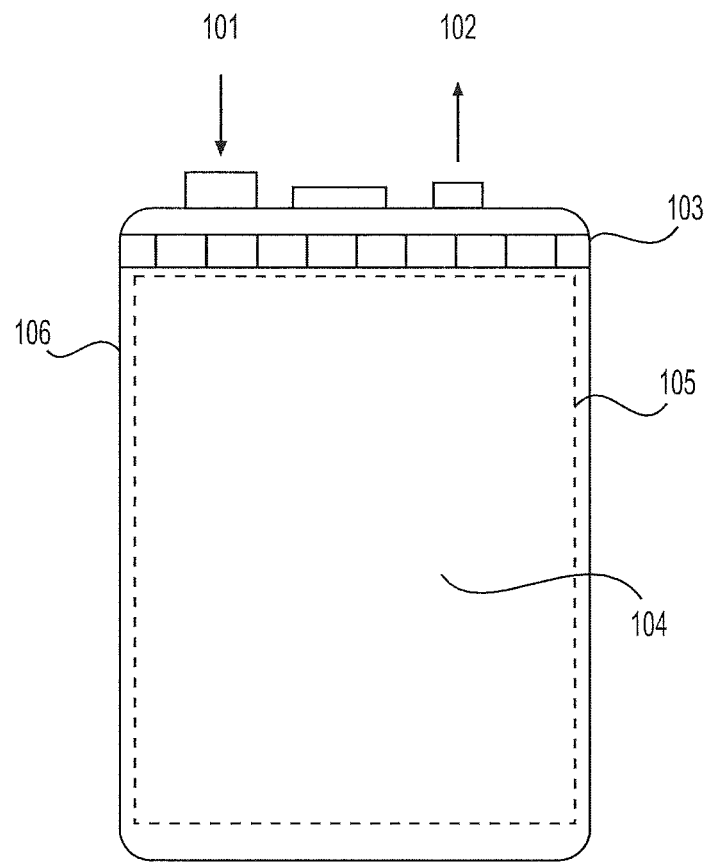
FIG. 1(a) is a front view of an embodiment of the lead exposure assessment device of the invention.

Reference will now be made in detail to the present embodiments of the present invention, examples of which are illustrated in the accompanying drawings, wherein like reference numerals refer to the like elements throughout. The embodiments are described below in order to explain the present invention by referring to the figures.

In one embodiment, the device of the invention may be connected at the point-of-use of an aqueous feed. For example, the device may be connected to a drinking water faucet in a place where people live or work. This includes but is not limited to a faucet in a home, a school, a library, a business, a store, or an office. Drinking water may be diverted through the device containing a cartridge which houses sampling media that removes lead particulate and soluble lead. Depending on the media used, other metals and chemicals of concern may be removed. In an embodiment of the invention, the device includes a flow totalizer that is configured to quantify the amount of water that passes though the device while accumulating lead. After a designated period of time, the detachable cartridge is removed from the device, packaged in shipping material, and shipped to a laboratory for analysis. The lead analysis results may be returned to the homeowner and reported as the average lead concentration, as calculated from the measure of total mass of lead in the cartridge and total water volume that passed through the device. The results provide a measurement of lead exposure from the tap water at the location, an indication of the extent to which the location has lead sources (e.g., lead service lines) and the corrosiveness of the tap water. An alternative use of the results would be for the identification of unseen lead service lines whereby a level above a field determined value would signify a high probability that a lead service line is present.

Broadly speaking, the device of the invention may be attached to a varied array of kitchen and other residential or commercial drinking water taps and can quantitatively trap lead and other metals while recording cumulative water use. The device may be easily disassembled and the detachable cartridge sent to a laboratory where the accumulated lead and other metals in the sampling media may be quantitatively recovered through appropriate chemical analysis techniques. Lead (and other contaminants) will be determined using a method common to the soils analysis and geology fields. For example, heat assisted acid digestion followed by inductively coupled plasma mass spectrometry (ICP-MS) analysis may be used as the basis of metal level determinations. Another analysis technique that may be used in determining the quantitative amount of lead and other metals is X-ray fluorescence (XRF).

One advantage of the invention is that lead (and other metals) may be passively accumulated over a measured cumulative volume of drinking water, and then directly analyzed by a laboratory to provide the amount of lead that would have been consumed at the tap, and the amount of lead per unit volume of water, an important exposure parameter for health and drinking water quality regulatory agencies. The device and method of the invention does not require residents to follow complicated sampling protocols to represent the lead that flows from the tap during typical water consumption at a particular location.

Turing to the drawings, FIG. 1(a) shows an embodiment of a lead exposure assessment device of the invention that includes an inlet 101 to receive a lead-containing aqueous feed and an outlet 102 to discharge a lead depleted treated aqueous feed. In this embodiment, housing 106 contains a cartridge 105, which is positioned so that the lead-containing aqueous feed passes from the inlet 101 through the cartridge to produce the lead depleted aqueous feed for discharge through the outlet 102. The cartridge contains sampling media 104. The housing 106 has a locking lid 103 that, with a proper tool, allows for easy access to the detachable cartridge 105 which houses media 104. The media 104 may then be extracted from the cartridge 105 for outside lead analysis, which may include analysis by a certified laboratory.

The device of the invention may be fitted directly on a faucet in a home or building. Although it is not shown in FIG. 1(a), the device may also include a flowmeter which is configured to provide the total flow of aqueous fluid through the device during a designated time period.

Figure 1B:
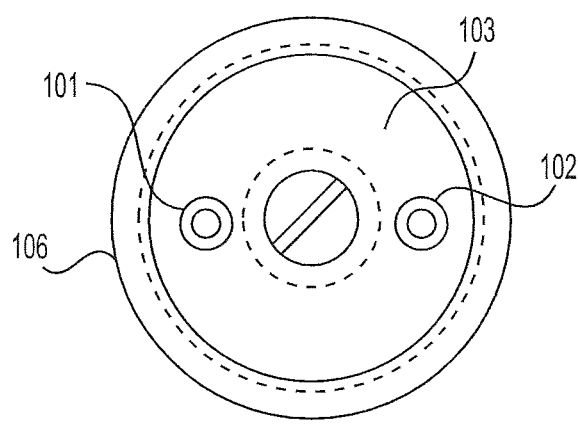
FIG. 1(b) is a top view of the same embodiment of the lead exposure assessment device provided in FIG. 1(a).

FIG. 1(b) is a top view of the lead exposure assessment device of the invention depicted in FIG. 1(a). FIG. 1(b) includes water inlet 101, water outlet 102, locking lid 103, and housing 106.

Figure 2:
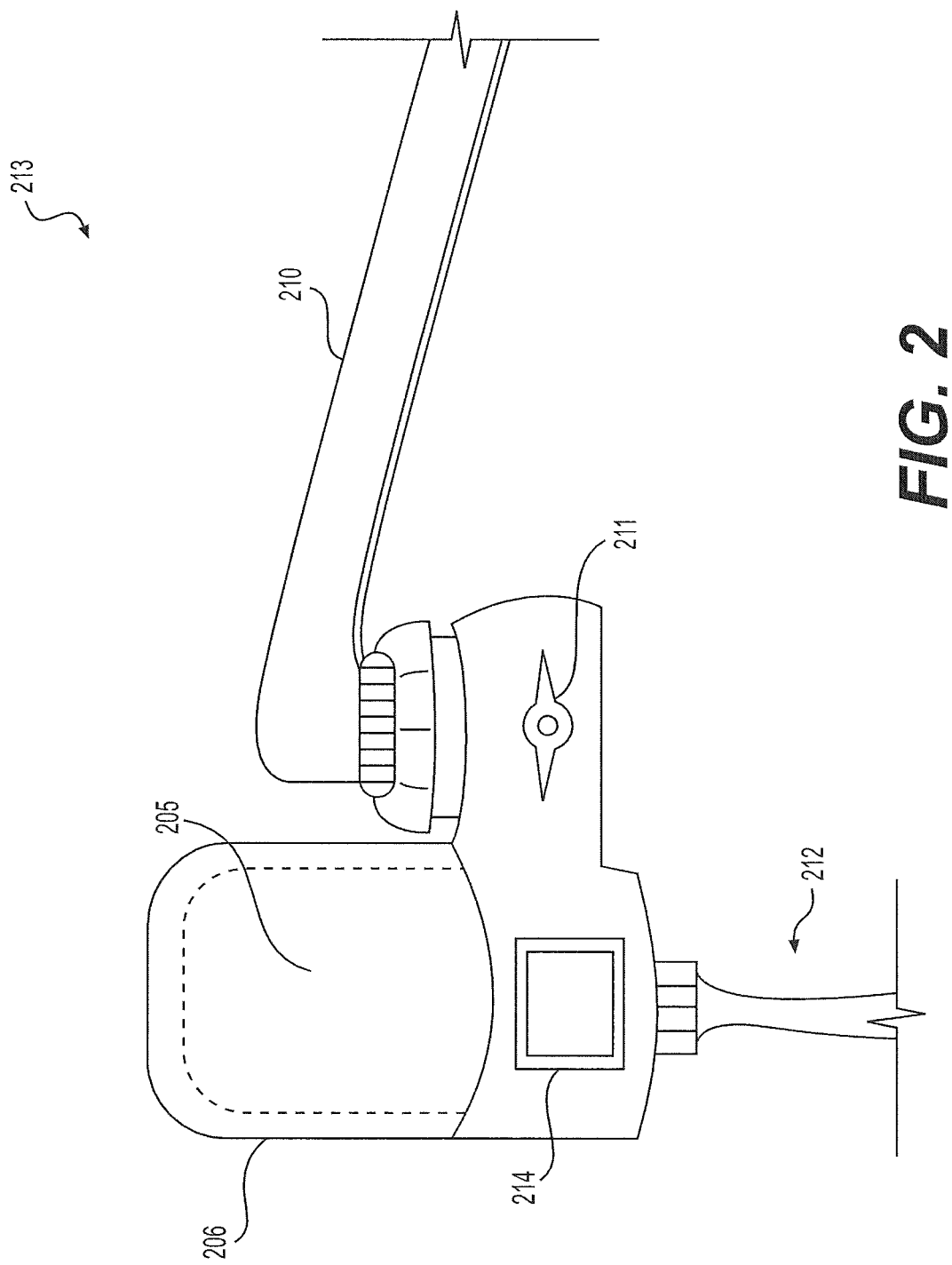
FIG. 2 is side view of an embodiment of the lead exposure assessment device of the invention, this embodiment including a totalizer flow meter.

FIG. 2 is side view of an embodiment of the lead exposure assessment device 213 of the invention, this embodiment including a totalizer flow meter 214. The device may be attached directly to a faucet 210 (e.g., a household faucet) via a common plumbing attachment (e.g., a threaded fitting). The device includes a bypass valve 211 which allows the flow to be diverted from the sampling meter during certain periods of time, such as when the media is being extracted for analysis. When the tap water is not being bypassed, it is directed though cartridge 205 located within the housing 206. The cartridge 205 contains sampling media, which captures the lead and other contaminants. The water is then directed though a totalizer flowmeter 214 that quantifies the flowrate and total flow through the media. Upon reaching a predetermined total flow, the cartridge containing sampling media may be removed, for example by unscrewing it from the device. The cartridge containing the media may then be sent to a certified laboratory for lead analysis (as well as analysis for other contaminants). After treatment, the water stream 212 may be consumed by the users.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A device comprising:
   (a) an inlet to receive a lead-containing aqueous feed;
   (b) an outlet to discharge a lead-depleted treated aqueous feed;
   (c) at least one cartridge positioned so that the lead-containing aqueous feed passes from the inlet and through the cartridge to produce the lead-depleted treated aqueous feed for discharge through the outlet,
   (d) a flowmeter configured to calculate the total flow of aqueous feed during a designated time period;
   (e) a flow totalizer configured to quantify the amount of water that passes through the device while lead is accumulated in the cartridge over a given period of time,
   wherein the cartridge contains sampling media,
   the lead comprises both particulate lead and soluble lead, and
   the device is configured to determine the average levels of lead in the aqueous feed, to quantify the average lead exposure of humans to the aqueous feed, to remove lead from the aqueous feed, and to identify the presence of lead service lines.

2. The device of claim 1, wherein the aqueous feed is drinking water.

3. The device of claim 2, wherein the device is adapted for attachment to at least one of a water faucet, a spigot, or another water outlet used for human consumption.

4. The device of claim 1, wherein the device removes metals in addition to lead.

5. The device of claim 4, wherein the device is configured to quantify the average exposure of humans to metals in addition to lead based on all water passing through the device.

6. The device of claim 1 wherein the sampling media comprises activated carbon, block carbon, resin-modified carbon or mixtures of the same.

7. The device of claim 1, wherein the sampling media may be extracted from the device for lead analysis.

8. A method of determining human exposure to lead in an aqueous feed over a designated time period, the method comprising: attaching the device of claim 1 to an aqueous feed outlet; determining the total flow of aqueous feed over the designated time period; removing the sampling media from the device after the designated time period; determining the amount of lead collected in the sampling media over the designated time period; calculating the average concentration of lead in the water by dividing the amount of lead by the total flow of aqueous feed.

9. The method of claim 8, wherein the aqueous feed is drinking water.

10. The method of claim 8, wherein the sampling media comprises activated carbon, block carbon, resin-modified carbon or mixtures of the same.

11. The method of claim 8, wherein the amount of lead collected in the sampling media is determined by heat assisted acid digestion followed by ICP-MS analysis.

12. The method of claim 8, wherein the method also determines human exposure to contaminants in addition to lead.

* * * * *